(12) United States Patent
Henderson

(10) Patent No.: US 7,135,056 B2
(45) Date of Patent: Nov. 14, 2006

(54) METHOD AND SYSTEM FOR SUB-AMBIENT PRESSURE CONTROL FOR COLUMN HEAD PRESSURE IN GAS CHROMATOGRAPHY SYSTEMS

(75) Inventor: Robert C. Henderson, Avondale, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 313 days.

(21) Appl. No.: 10/777,665

(22) Filed: Feb. 13, 2004

(65) Prior Publication Data

US 2005/0178266 A1 Aug. 18, 2005

(51) Int. Cl.
*B01D 53/02* (2006.01)

(52) U.S. Cl. .............................. 95/82; 96/102; 96/103; 73/23.35; 73/23.36; 73/23.42

(58) Field of Classification Search ................ 95/82, 95/89; 96/101, 102, 103; 73/23.35, 23.36, 73/23.42
See application file for complete search history.

(56) References Cited

U.S. PATENT DOCUMENTS

| 4,141,237 A | 2/1979 | DeFord et al. |
| 5,952,556 A | 9/1999 | Shoji |
| 2003/0126908 A1 | 7/2003 | Furukawa |

FOREIGN PATENT DOCUMENTS

JP          2001305118 A    *  10/2001

* cited by examiner

*Primary Examiner*—Robert A. Hopkins

(57) ABSTRACT

Methods and system for sub-ambient pressure control for column head pressure in gas chromatography (GC) systems. The GC system includes an inlet and a capillary column connected to the inlet. The inlet includes a valve that regulates an inlet pressure and pressure sensor that measures the inlet pressure and outputs a signal that indicates a measured inlet pressure. The GC system also includes an inlet-pressure set-point that can be set to a negative pressure set-point representing a pressure below ambient pressure, the negative pressure set-point driving the valve to change the inlet pressure until the measured inlet pressure equals the negative pressure set-point.

20 Claims, 4 Drawing Sheets

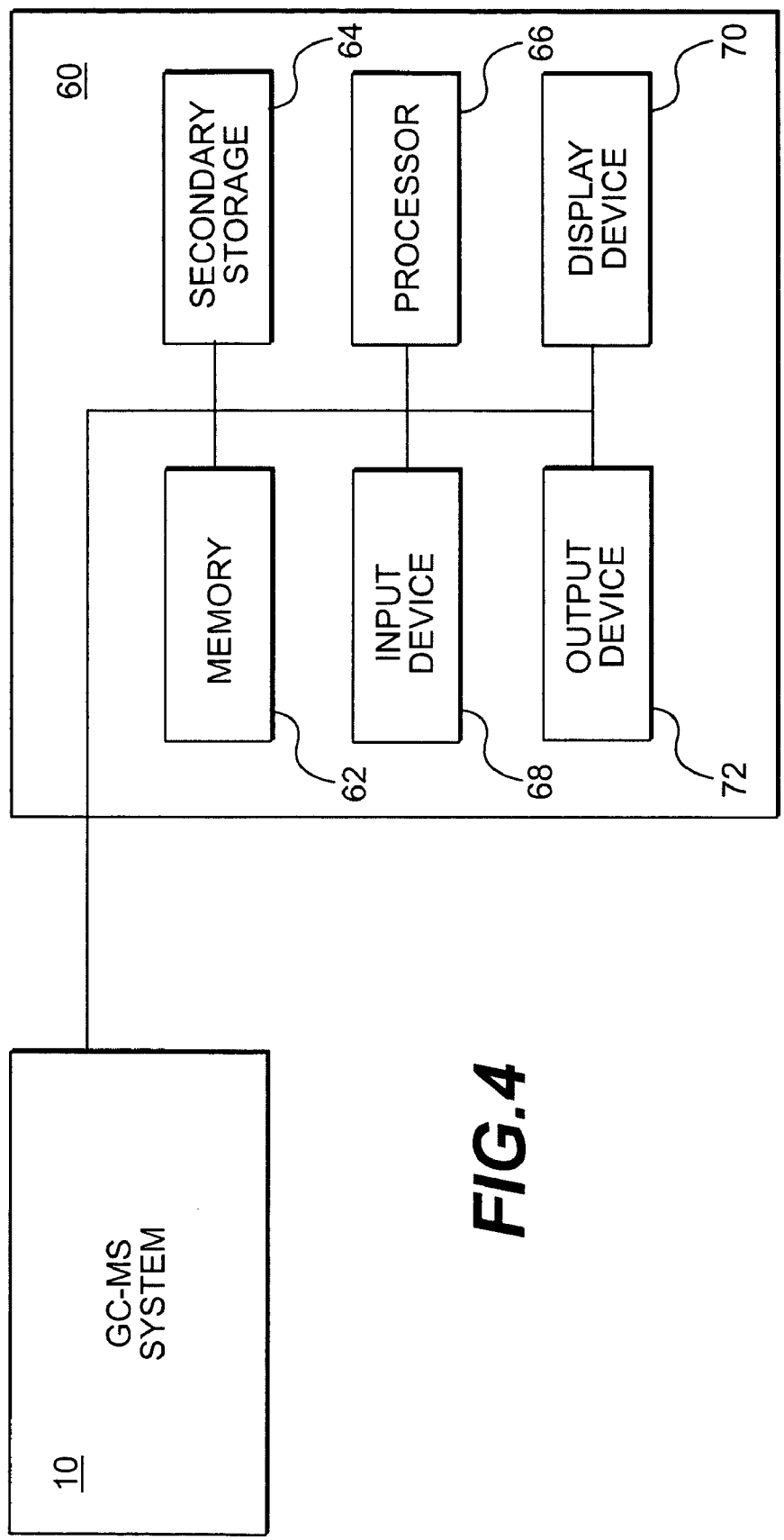

METHOD AND SYSTEM FOR SUB-AMBIENT PRESSURE CONTROL FOR COLUMN HEAD PRESSURE IN GAS CHROMATOGRAPHY SYSTEMS

BACKGROUND

In a typical Gas Chromatography (GC) system, a capillary column is connected from the inlet of the GC to a Mass Spectrometer (MS). GC-MS systems are operated in a vacuum outlet condition. When the GC-MS system is operated in this vacuum outlet condition, the optimum pressure at the inlet to the column can be very low. Theoretically, the optimum inlet pressure should be set so low that it would go negative relative to ambient pressure.

Electronic pressure control is common in current GCs. Pressure set-points are entered in gauge pressures (pressure relative to ambient pressure) using the electronic pressure control. Unfortunately, existing electronic pressure controllers in GCs do not allow negative pressure (relative to ambient pressure) set-points. Consequently, it is necessary in existing GC-MS systems to maintain a positive inlet gauge pressure set-point and a resultant positive inlet pressure. Column flow in the capillary column is proportional (i.e., a squared relationship) to the inlet pressure when the GC-MS system is operated in a vacuum outlet condition. As a result, maintaining a positive inlet gauge pressure causes a higher column flow than is actually desired. As shown by the Van Deemter-plot in FIG. 1, the higher column flow, measured as an average linear velocity, above a certain level results in a reduced efficiency (lower HETP=greater efficiency) for mass spectrometry. FIG. 1 shows that for the specified column, conditions, and chemical (carrier gas), an average linear velocity of between approximately 20–30 cm/sec results in the greatest efficiency.

SUMMARY

What are described are a method and system for sub-ambient pressure control for column head pressure in a gas chromatography (GC) system. The GC system includes an inlet and a capillary column connected to the inlet. The inlet includes a valve that regulates an inlet pressure and pressure sensor that measures the inlet pressure and outputs a signal that indicates a measured inlet pressure. The GC system also includes an inlet-pressure set-point that can be set to a negative pressure set-point representing a pressure below ambient pressure, the negative pressure set-point driving the valve to change the inlet pressure until the measured inlet pressure equals the negative pressure set-point.

DESCRIPTION OF THE DRAWINGS

FIG. 4 is a block diagram illustrating an embodiment of a system for sub-ambient pressure control with an attached computer.

DETAILED DESCRIPTION

Figure 2:
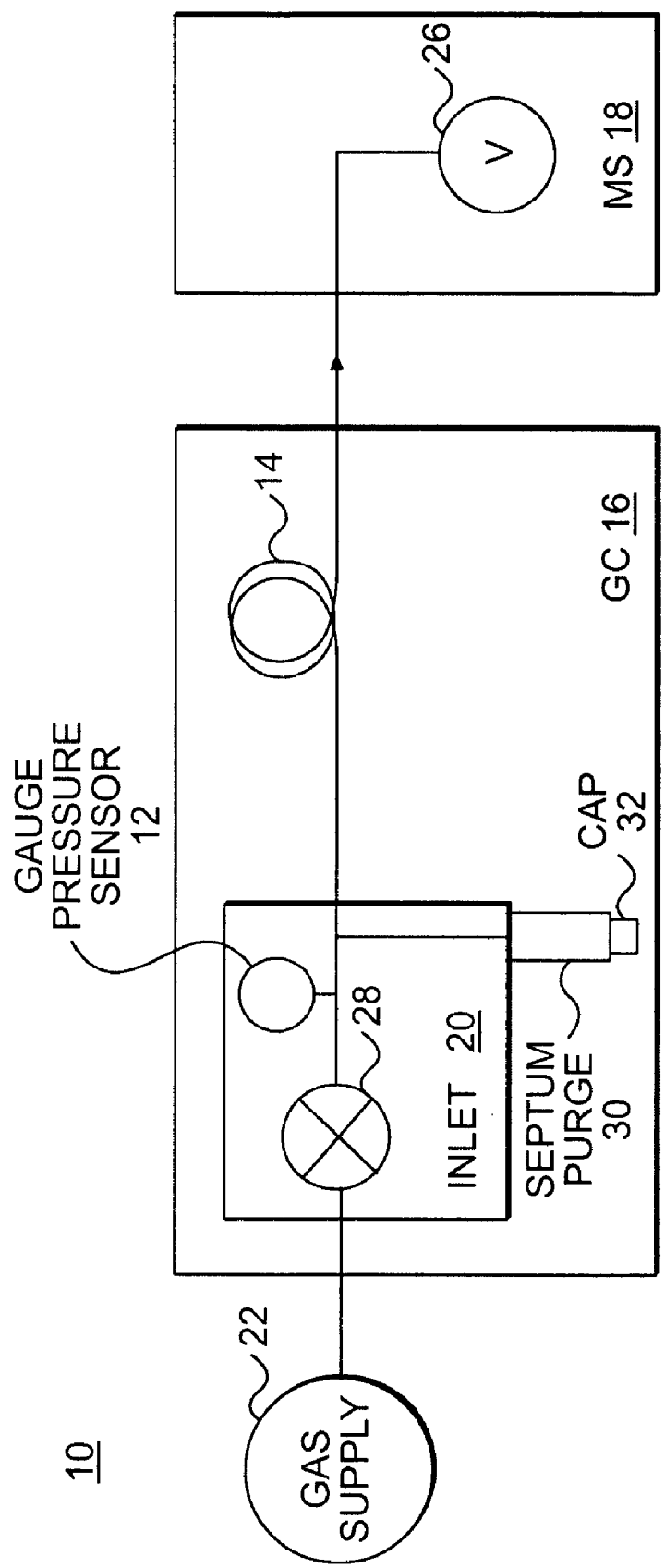
FIG. 2 is a block diagram illustrating an embodiment of a system for sub-ambient pressure control.

FIG. 2 is a block diagram of an embodiment of a GC-MS system 10 for sub-ambient pressure control. The GC-MS system 10 includes a gauge pressure sensor 12 that measures the inlet pressure into a capillary column 14. Gauge pressure sensors in most GC-MS systems are piezo-resistive based. Typically, the strain-sensitive resistances in a piezo-resistive based gauge pressure sensor are deposited on a thin diaphragm in a bridge arrangement. In a gauge pressure sensor, the measured pressure is on one side of the diaphragm and ambient pressure is on the other side of the diaphragm. The stresses induced on the diaphragm by a differential pressure across the diaphragm can be measured as a voltage signal. The voltage signal is amplified and then input into an analog to digital converter (ADC) for conversion to a digital signal that can be used by electronics controlling the GC-MS system. These electronics may include an electronic pressure control.

Inlets in GC-MS systems may also include software and electronics (e.g., circuitry) that enable the setting of an inlet pressure set-point. If the inlet pressure measured by the gauge pressure sensor does not equal the inlet pressure set-point, the software and electronics cause the inlet to increase or decrease the inlet pressure until it matches the inlet pressure set-point.

Generally, such gauge pressure sensors are bi-directional and can sense positive and negative differential pressures (e.g., measured pressure can be greater than or less than ambient pressure) producing a positive and negative voltage signal, respectively. However, existing GC-MS systems do not allow a negative voltage signal to be input to the ADC, as the treatment of negative voltage signals is substantially more complicated. This is one reason why existing GC-MS systems do not allow negative (relative to ambient) pressure set-points at the column inlet.

In GC-MS systems used over time, various system degradation factors can arise (e.g., wear, temperature shifts, long term drift, etc.) that cause the gauge pressure sensors to inadvertently produce a negative voltage that is input into the ADC. To avoid this, the electronics that amplify the voltage signal in many gauge pressure sensors include an offset in their output so that a zero pressure differential across the diaphragm equals some positive offset voltage at the output. A typical offset is Gauge Pressure In=0 psig (zero pressure differential), Voltage Out=1 volt. By including the offset, the gauge pressure sensor avoids inadvertently inputting negative voltage signals into the ADC.

It was determined that, if the offset is sufficiently large enough, then a positive voltage signal could still be produced with a negative gauge pressure. A Gauge Pressure In=0 psig indicates that the pressure on both sides of the diaphragm is ambient pressure. Ambient pressure typically equals approximately 14.7 psia, although the ambient pressure may vary depending on altitude and other factors. A typical gauge pressure sensor with a 1 v offset may have a range of 0 psig–100 psig Gauge Pressure In and a range of 1v–4v Voltage Out. In such a gauge pressure sensor, therefore, there is approximately 33.3 psig per volt. Consequently, still avoiding a negative voltage, a minimum Voltage Out of 0 v would equal −33.3 psig. However, assuming an ambient pressure of 14.7 psia, the maximum possible negative Gauge Pressure In=−14.7 psig. This maximum negative Gauge Pressure In of −14.7 psig will produce a minimum voltage out of approximately 0.56 v (i.e., 1 v−(14.7 psig/33.3 psig/v)).

A minimum voltage out of 0.56 v provides a sufficiently large enough margin to avoid inadvertently producing negative voltages in gauge pressure sensors due to the various factors discussed above. Further, a GC-MS system will only be able to achieve the maximum possible negative Gauge Pressure In of −14.7 psig, and the resultant minimum Voltage Out of 0.56 v, if the GC-MS system 10 is perfectly sealed and contains no leaks. In practice, the inlet will be at some pressure above this (to allow flow through the column), so that some small, finite leaks may be acceptable, as long as the pressure setpoint can be achieved in the inlet. Moreover, since the ADC will always see a positive voltage, and since increasing absolute pressure always translates to increasing voltage at the ADC input, a GC-MS system 10 allowing negative pressure set-points according to the above principles determined by the inventor does not require any additional components ordinarily necessary to treat negative voltages.

With reference again to FIG. 2, a GC-MS system 10 allowing negative pressure set-points according to the above principles is shown. The GC-MS system 10 with sub-ambient pressure control includes a GC 16 connected to a MS 18. The GC 16 includes a GC inlet 20 and the capillary column 14. In operation, a gas supply 22 is connected to the GC inlet 20. The GC-MS system 10 operates in a vacuum outlet condition on the capillary column 14. Accordingly, the MS 18 includes a vacuum pump 26.

The GC inlet 20 includes a proportional valve 28 and the gauge pressure sensor 12. The GC inlet 20 also may include control electronics, additional hardware (e.g., a processor, memory, etc.) and/or software (not shown) that cause the proportional valve 28 to increase or decrease the inlet pressure based on the gauge pressure determined by the gauge pressure sensor and an inlet pressure set-point. Alternatively, this hardware and/or software may be located elsewhere in the GC-MS system 10 or in an attached computer (not shown). Further, in order to achieve the desired negative inlet pressures, leaks in the GC-MS system 10 are minimized. Normally, GC inlets include a septum purge to sweep away contamination from the septum (an elastomeric disc through which the sample is injected into the inlet) so that the contaminants do not appear in the GC analysis. Consequently, the GC inlet 20 includes a cap 32 on a septum purge 30 in order to minimize leaks through the septum purge 30. Alternatively, the GC inlet 20 does not have the septum purge 30. The use of a septum purge is optional and is dependent on the application.

With continued reference to FIG. 2, the GC-MS system 10, in the GC inlet 20 or elsewhere, and/or an attached computer, also includes software for setting the inlet pressure set-point. Alternatively, the GC inlet 20 may also include electronics for setting the inlet pressure set-point. The inlet pressure set-point is typically set in response to a user or computer program input indicating the desired set-point. In operation, a user or computer program inputs a desired set-point as a pressure in relative to ambient. The GC-MS system 10 or the attached computer set the inlet pressure set-point to the desired value. The inlet pressure set-point is set as a voltage signal that equals the voltage out signal produced by the gauge pressure sensor 12 when the inlet pressure equals the desired set-point.

The gauge pressure sensor 12 continuously measures the inlet pressure and produces a corresponding voltage out signal. The GC-MS system 10 or the attached computer read the measured inlet pressure from the gauge pressure sensor 12 and compare the measured inlet pressure to the inlet pressure set-point. In other words, the voltage out signal produced by the gauge pressure sensor is compared to the inlet pressure set-point voltage signal. The comparison may be performed software and/or control electronics. For example, the control electronics may include an error amplifier and a voltage comparator that produces a negative voltage signal if the inlet pressure set-point is less than the measured inlet pressure and a positive voltage signal if the inlet pressure set-point is greater than the measured inlet pressure. If these voltages differ, i.e., if the measured inlet pressure is different then the inlet pressure set-point, then the GC-MS system 10 or the attached computer cause the proportional valve 28 to change the inlet pressure until the inlet pressure matches the inlet pressure set-point. The proportional valve 28 opens more to increase the inlet pressure and closes more to decrease the inlet pressure. For example, a positive voltage signal (e.g., from the control electronics or the software) may increasingly drive the proportional valve 29 (i.e., causing it to open more) and a negative voltage may decreasingly drive the proportional valve (i.e., causing it to close more).

With continued reference to FIG. 2, the GC-MS system 10 allows the inlet pressure set-point to be set to a negative pressure (relative to ambient). The lack of a septum purge 30 or the cap 32 on the septum purge 30 enable the vacuum pump 26 to draw the inlet pressure below ambient. Moreover, the gauge pressure sensor 12 includes an offset that enables positive voltage out values for negative pressure in values. The user inputs a desired negative pressure set-point. As above, the GC-MS system 10 and/or the attached computer set the inlet pressure set-point to the desired negative pressure set-point. Per the above-described principles, the voltage of the inlet pressure set-point corresponding to the desired negative pressure set-point is still a positive voltage due to the offset. The GC-MS system 10 and/or the attached computer treat this inlet pressure set-point as any other inlet pressure set-point, causing the proportional valve 28 to change the inlet pressure until it matches the inlet pressure set-point.

Figure 1:
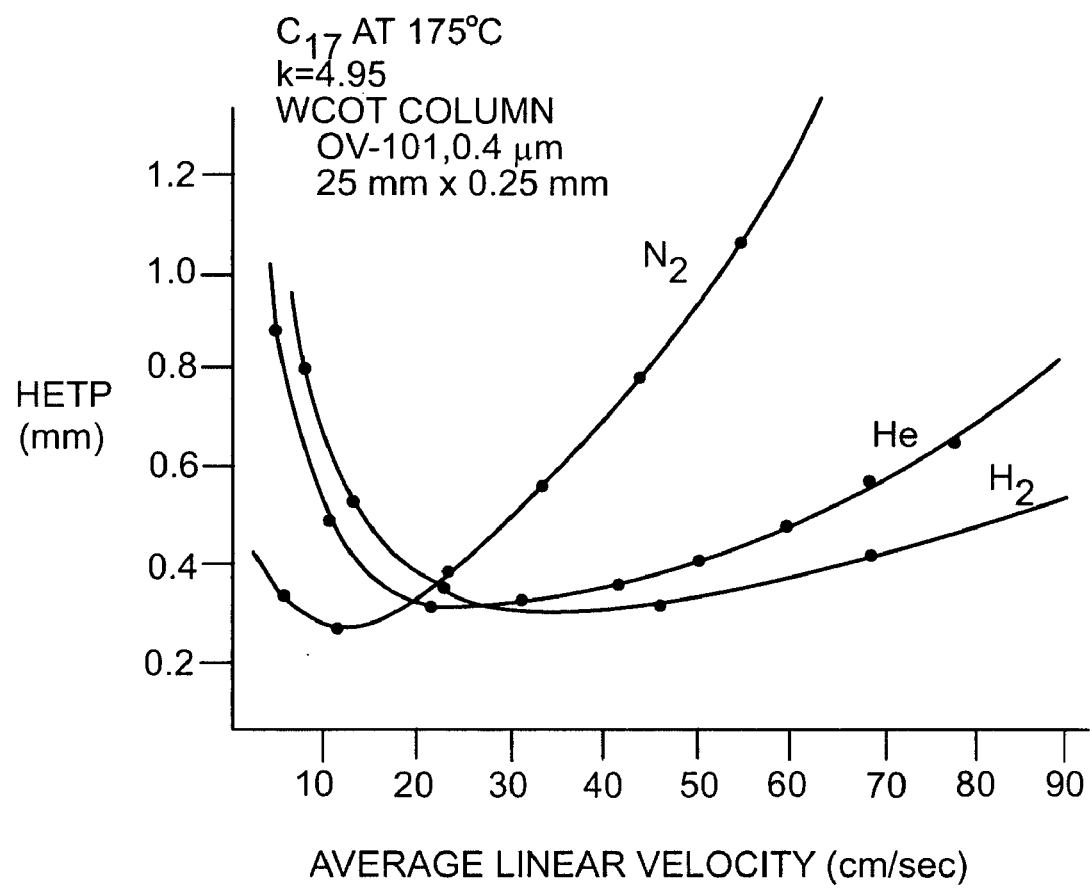
FIG. 1 is a Van Deemter-plot illustrating efficiency curves for a capillary column with hydrogen, helium and nitrogen carrier gases.

TABLE 1 below illustrates the improved efficiency utilizing the GC-MS system 10 with sub-ambient pressure control. The carrier gas in TABLE 1 is Helium. The positive inlet pressure (head pressure) in an existing system requires a column flow (Flow Rate) of 3 mLn/min and an average linear velocity of 87.86 cm/sec. The negative inlet pressure enabled by the GC-MS system 10, however, only produces a column flow of 1.28 mLn/min and an average linear velocity of 57.39 cm/sec. With reference again to FIG. 1, the 57.39 cm/sec average linear velocity produced by the GC-MS system 10 is significantly more efficient than the 87.86 cm/sec produced by the existing system. The capillary column used in both examples shown below had a length of 15 m, an internal diameter of 320 µm, and a file thickness and phase ratio of 0.500 µm and 160.0, respectively.

TABLE 1

|  | Prior Art | GC-MS System |
| --- | --- | --- |
| Carrier Gas | Helium | Helium |
| Head Pressure, psi | 1.526 | −4.100 |
| Flow Rate, mLn/min | 3 | 1.2800 |
| Outlet Velocity, cm/sec | Very large | Very large |
| Average Velocity, cm/sec | 87.86 | 57.39 |
| Hold-up Time, min | 0.284538 | 0.435609 |
| Outlet Pressure (absolute), psi | 0 | 0 |
| Ambient Pressure (absolute), psi | 14.696 | 14.696 |

Figure 3:
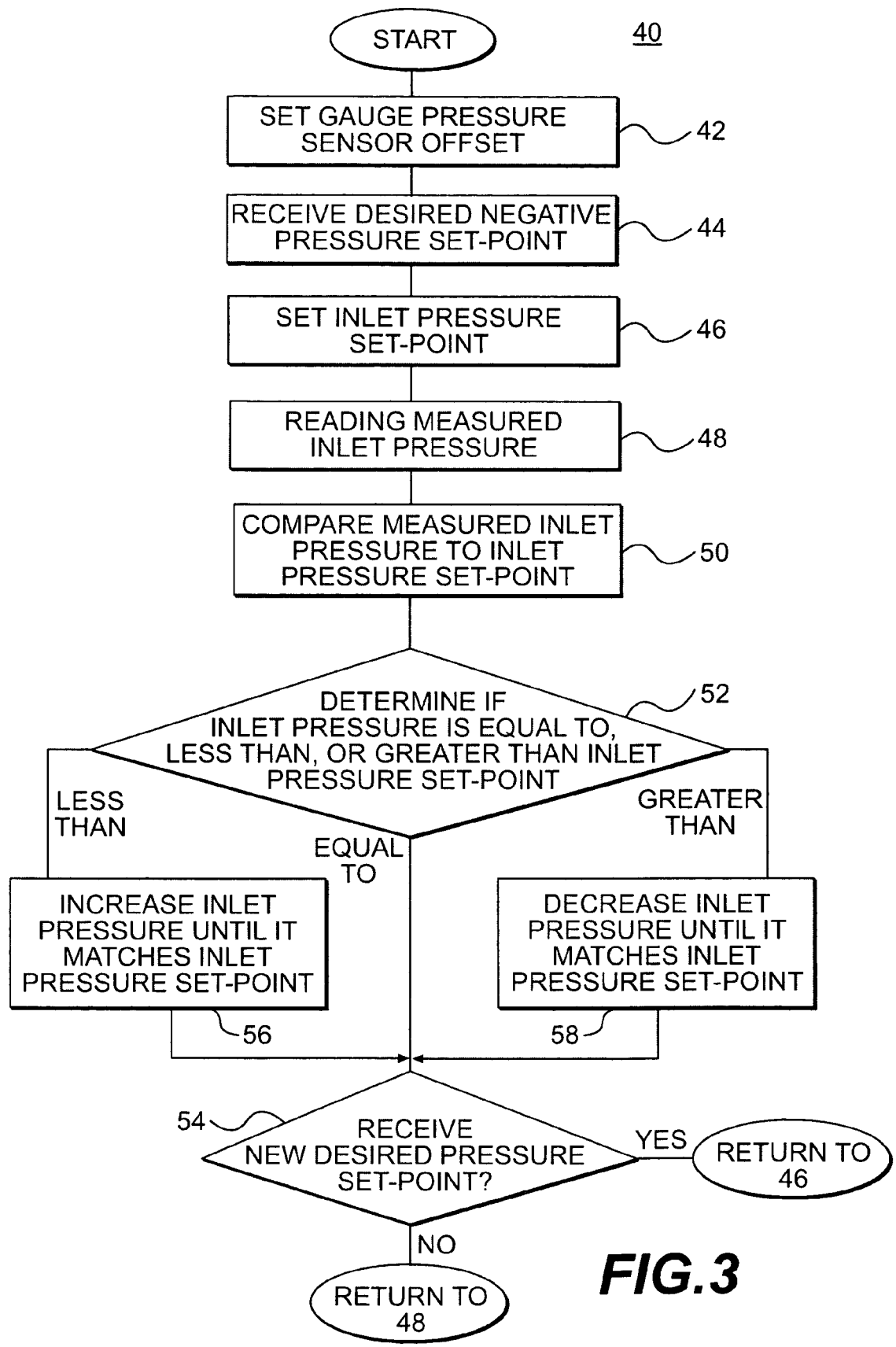
FIG. 3 is a flowchart illustrating an embodiment of a method for sub-ambient pressure control.

With reference now to FIG. 3, shown is a flowchart illustrating a method 40 with sub-ambient pressure control in GC-MS systems. The method 40 includes setting a gauge pressure sensor offset, block 42. As discussed above, the gauge pressure sensor offset should be large enough to enable a −14.7 psig inlet pressure set-point and still provide a sufficient margin of error to avoid a negative voltage out due to the system degradation factors described above. If the gauge pressure sensor already includes an offset that is sufficiently large enough, then block 42 may be skipped.

The method 40 further includes receiving a desired negative pressure set-point, block 44. The desired negative pressure set-point may be input, for example, by a user or a computer program. The method 40 sets the inlet pressure set-point to the desired negative pressure set-point, block 46. The inlet pressure set-point is set as a voltage that equals the voltage out produced by the gauge pressure sensor when the inlet pressure equals the desired set-point.

If an existing GC-MS system does not enable a user to enter negative set-points, the method 40 may also include a step (not shown) of modifying the GC-MS system to enable a negative set-point. Such a step may include enabling a voltage out that is less than the gauge pressure sensor offset voltage and enabling the inlet pressure set-point to be set to a voltage below the gauge pressure sensor offset voltage. This step may be achieved by modifying software in the existing GC-MS system or in an attached computer.

With continued reference to FIG. 3, the method 40 includes reading the measured inlet pressure, block 48. The inlet pressure may be measured by a gauge pressure sensor. The method 40 compares the measured inlet pressure to the inlet pressure set-point, block 50. This may be achieved by comparing the voltage out produced by the gauge pressure sensor to the inlet pressure set-point voltage. The method determines if the measured inlet pressure is equal to, less than, or greater than the inlet pressure set-point, block 52. If the measured inlet pressure is equal to the inlet pressure set-point, the method 40 returns to block 48, unless a new desired set-point is received, block 54.

If the measured inlet pressure is less than the inlet pressure set-point, the method 40 causes the proportional valve 28 to increase the inlet pressure until it matches the inlet pressure set-point, block 56. The proportional valve 28 functions as a variable pneumatic restriction. Opening the proportional valve 28 more (i.e., reducing the proportional valve's restriction) will allow more molecules from the gas supply 22 to reach the inlet 20), thus raising the inlet pressure. Closing the proportional valve 28 has the opposite effect. If the measured inlet pressure is greater than the inlet pressure set-point, the method 40 causes the proportional valve to decrease the inlet pressure until it matches the inlet pressure set-point, block 58. In either case, the method 40 returns to block 48, unless a new desired set-point is received, block 48.

With reference now to FIG. 4, shown is a block diagram illustrating the GC-MS system 10 for sub-ambient pressure control with an exemplary attached computer 60. The attached computer 60 may be connected with the GC-MS system 10 using any communication medium, such as a direct peripheral device connection, an Ethernet connection, a LAN, the Internet, etc.

Computer 60 typically includes a memory 62, a secondary storage device 64, a processor 66, an input device 68, a display device 70, and an output device 72. Memory 62 may include RAM or similar types of memory, and memory 62 may store one or more applications for execution by processor 66. These applications may include the software described above. Secondary storage device 64 may include a hard disk drive, floppy disk drive, CD-ROM drive, or other types of non-volatile data storage. Processor 66 executes the application(s), which is stored in memory 62 or secondary storage 64, or received from the Internet or other network. Input device 68 may include any device for entering information into computer 60, such as a keyboard, mouse, cursor-control device, touch-screen, microphone, digital camera, video recorder or camcorder. Display device 70 may include any type of device for presenting visual information such as, for example, a computer monitor or flat-screen display. Output device 72 may include any type of device for presenting a hard copy of information, such as a printer, and other types of output devices include speakers or any device for providing information in audio form.

Computer 60 may store a database structure in secondary storage 64, for example, for storing and maintaining information need or used by the application(s). Also, processor 66 may execute one or more software applications in order to provide the functions described in this specification, specifically in the methods described above, and the processing may be implemented in software, such as software modules, for execution by computers or other machines. The processing may provide and support GUIs. The GUIs may be formatted, for example, as web pages in HyperText Markup Language (HTML), XML or in any other suitable form for presentation on a display device.

Although computer 60 is depicted with various components, one skilled in the art will appreciate that the servers can contain additional or different components. In addition, although applications, instructions, software, modules, etc., for performing the above-described functions are described as being stored in memory, one skilled in the art will appreciate that these applications, instructions, software, modules, etc., can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling a system, such as GC-MS system 10, to perform a particular method. Further, the memory 62 and/or secondary storage 64 may include instructions for performing the steps described above with reference to FIGS. 2 and 3. These instructions may also include instructions for providing a user with a GUI for inputting desired negative (and positive) pressure set-points, displaying the measured inlet pressure and otherwise operating the GC-MS system 10. Further, these instructions may also include a computer program for specifying the desired pressure set-points, as described above, per a set testing procedure or other algorithm.

The above GC-MS system 10 for sub-ambient pressure control has been described as enabling a negative pressure (relative to ambient) set-point. A negative pressure relative to ambient is equivalent to an absolute pressure greater than zero that is less than ambient. In other words, a pressure in=−5 psig is equivalent to a pressure in=9.7 psia, if ambient is 14.7 psia. Further, ambient pressure may also be measured as 1 atmosphere. In such a case, a negative pressure would be indicated as less than 1 atmosphere. Additionally, there are other units for measuring pressure. Consequently, the GC-MS system 10 and the method 40 for sub-ambient pressure control may be modified to measure and controlling pressure as an absolute pressure, a pressure in atmospheres, or any other units, or according to any manner for measuring and indicating pressure, in addition to or instead of measuring and controlling pressure relevant to ambient where 0 psig=14.7 psia. For example, the GC-MS system 10 and the method 40 may enable the desired pressure set-point to be input as an absolute pressure that is less than ambient.

For example, an alternative embodiment of the GC-MS system 10 includes an absolute pressure sensor as a replacement for the gauge pressure sensor 12 in the GC inlet 20. In this embodiment, the absolute inlet pressure would be measured directly, so set-points below ambient pressure would still be represented as a positive pressure. With the absolute pressure sensor, the set-point may be represented as an absolute pressure instead of a negative gauge pressure. For example, if ambient pressure was 14.7 psia, a negative gauge set-point of −5 psig would be the same as a set-point of 9.7 psia. In this embodiment, the electronic controls for controlling the proportional valve 28 would be connected to the absolute pressure sensor. The electronic controls would control the proportional valve 28 based on a comparison of the absolute pressure calculations and the absolute pressure set-point.

The foregoing description provides illustration and description, but is not intended to be exhaustive or to limit the invention to the embodiments disclosed. Modifications and variations are possible consistent with the above teachings or may be acquired from practice of the embodiments disclosed. Therefore, it is noted that the scope is defined by the claims and their equivalents.

The invention claimed is:

1. A system for sub-ambient pressure control for column head pressure in a gas chromatography (GC) system, comprising:
    an inlet including:
        a valve that regulates an inlet pressure; and
        a pressure sensor that measures the inlet pressure and outputs a signal that indicates a measured inlet pressure, wherein the inlet includes an inlet-pressure set-point that can be set to a negative pressure set-point representing a pressure below ambient pressure, the negative pressure set-point driving the valve to change the inlet pressure until the measured inlet pressure equals the negative pressure set-point; and
    a capillary column connected to the inlet.

2. The system of claim 1, further comprising:
    a mass spectrometer (MS) connected to the capillary column.

3. The system of claim 1, wherein the inlet further includes:
    an electronic pressure controller that drives the valve in response to the inlet-pressure set-point and the measured inlet pressure.

4. The system of claim 1, wherein the pressure sensor is a gauge pressure sensor.

5. The system of claim 1, wherein the GC includes instructions on a computer-readable medium for:
    setting the inlet-pressure set-point to a negative pressure set-point; and
    driving the valve to change the inlet pressure until the measured inlet pressure equals the negative pressure set-point.

6. The system of claim 1, wherein the inlet includes an error amplifier that receives the measured inlet pressure signal and an inlet-pressure set-point signal and outputs a decreasing drive to the valve when the inlet-pressure set-point signal is less than the measured inlet pressure signal.

7. The system of claim 6, wherein the error amplifier outputs an increasing drive to the valve that causes the valve to increase the inlet pressure.

8. The system of claim 2, wherein the MS includes a vacuum pump connected to the capillary column.

9. The system of claim 1, wherein the inlet further includes:
    a septum purge; and
    a cap on the septum purge.

10. The system of claim 1, further comprising:
    a computer, connected to the GC, including:
        a processor; and
        a memory that includes instructions executed by the processor for:
            setting the inlet-pressure set-point to a negative pressure set-point; and
            causing the valve to change the inlet pressure until the measured inlet pressure equals the negative pressure set-point.

11. A system for sub-ambient pressure control for column head pressure in a gas chromatography (GC) system, comprising:
    an inlet including:
        a valve that regulates an inlet pressure; and
        a pressure sensor that measures the inlet pressure and outputs a signal that indicates a measured inlet pressure, wherein the inlet includes an inlet-pressure set-point that can be set to a negative pressure set-point representing a pressure below ambient pressure, the negative pressure set-point driving the valve to change the inlet pressure until the measured inlet pressure equals the negative pressure set-point and wherein the gauge pressure sensor includes an offset (vo) so that a measured inlet pressure of zero (0 psig) causes the gauge pressure sensor to output a positive measured inlet pressure voltage (vo, where vo>0 volts); and a capillary column connected to the inlet.

12. The system of claim 11, wherein the offset is 1 volt (vo=1 volt).

13. The system of claim 11, wherein the offset is large enough to avoid the gauge pressure sensor inadvertently outputting a negative measured inlet pressure voltage.

14. A method for sub-ambient pressure control for column head pressure in a gas chromatography (GC) system comprising:
    receiving a desired negative pressure set-point representing a pressure below ambient pressure; and
    setting an inlet pressure set-point to the desired negative pressure set-point, wherein the desired negative pressure set-point indicates a desired negative inlet pressure for an inlet of the GC.

15. The method of claim 14, further comprising:
    reading a measured inlet pressure, wherein the measured inlet pressure is measured by a gauge pressure sensor in an inlet of the GC;
    comparing the measured inlet pressure to the inlet pressure set-point;
    determining if the measured inlet pressure is greater than the inlet pressure set-point; and
    if the measured inlet pressure is greater than the inlet pressure set-point, decreasing the inlet pressure until the inlet pressure is a negative pressure matching the inlet pressure set-point.

16. The method of claim 14, further comprising:
    if the measured inlet pressure is less than the inlet pressure set-point, increasing the inlet pressure until the inlet pressure is a negative pressure matching the inlet pressure set-point.

17. The method of claim 15, wherein the decreasing step includes causing a proportional valve in the inlet of the GC to decrease the inlet pressure.

18. A method for sub-ambient pressure control for column head pressure in a gas chromatography (GC) system comprising:
    receiving a desired negative pressure set-point representing a pressure below ambient pressure;
    setting an inlet pressure set-point to the desired negative pressure set-point, wherein the desired negative pressure set-point indicates a desired negative inlet pressure for an inlet of the GC; and
    setting a gauge pressure sensor offset (vo) so that a measured inlet pressure of zero (0 psig) causes a gauge pressure sensor to output a positive measured inlet pressure voltage (vo, where vo>0 volts).

19. A computer-readable medium comprising instructions for providing sub-ambient pressure control for column head pressure in a gas chromatography (GC) system by:
    receiving a desired negative pressure set-point representing a pressure below ambient pressure; and
    setting an inlet pressure set-point to the desired negative pressure set-point, wherein the desired negative pressure set-point indicates a desired negative inlet pressure for an inlet of the GC.

20. The computer-readable medium of claim 19, further comprising instructions for:
    reading a measured inlet pressure, wherein the measured inlet pressure is measured by a gauge pressure sensor in an inlet of the GC;
    comparing the measured inlet pressure to the inlet pressure set-point;
    determining if the measured inlet pressure is greater than the inlet pressure set-point; and
    if the measured inlet pressure is greater than the inlet pressure set-point, decreasing the inlet pressure until the inlet pressure is a negative pressure matching the inlet pressure set-point.

* * * * *